United States Patent
Whalen et al.

(10) Patent No.: US 10,632,444 B2
(45) Date of Patent: Apr. 28, 2020

(54) BIOLOGICAL SAMPLE ANALYTICAL INSTRUMENT

(71) Applicant: Douglas Scientific, LLC, Alexandria, MN (US)

(72) Inventors: Mark Whalen, Alexandria, MN (US); Charles Gervais, Alexandria, MN (US); Anthony Sanborn, Farwell, MN (US); Andrew Haug, Alexandria, MN (US); Darren Cook, Alexandria, MN (US); Satish Rai, Sartell, MN (US); Hans A. Mische, Grey Eagle, MN (US); Stephen A. Judice, Dayton, ME (US); Daniel J. Shaffer, South Portland, ME (US)

(73) Assignee: DOUGLAS SCIENTIFIC, LLC, Alexandria, MN (US)

( * ) Notice: Subject to any disclaimer, the term of this patent is extended or adjusted under 35 U.S.C. 154(b) by 412 days.

(21) Appl. No.: 14/760,416

(22) PCT Filed: Jan. 13, 2014

(86) PCT No.: PCT/US2014/011267
§ 371 (c)(1),
(2) Date: Jul. 10, 2015

(87) PCT Pub. No.: WO2014/110494
PCT Pub. Date: Jul. 17, 2014

(65) Prior Publication Data
US 2015/0352512 A1 Dec. 10, 2015

Related U.S. Application Data

(60) Provisional application No. 61/751,470, filed on Jan. 11, 2013.

(51) Int. Cl.
*B01J 19/00* (2006.01)
*B01L 7/00* (2006.01)
(Continued)

(52) U.S. Cl.
CPC ............ *B01J 19/0046* (2013.01); *B01L 7/00* (2013.01); *C12Q 1/6846* (2013.01);
(Continued)

(58) Field of Classification Search
CPC .......... B01J 19/0046; B01J 2219/00585; B01J 2219/00351; B01J 2219/00313;
(Continued)

(56) References Cited

U.S. PATENT DOCUMENTS 3,620,678 A * 11/1971 Guigan .................. B01L 3/505
422/66
3,810,806 A * 5/1974 Swartz .................... B29C 65/18
156/498

(Continued)

FOREIGN PATENT DOCUMENTS

| EP | 1249702 A1 | 10/2002 |
|---|---|---|
| WO | 2010039926 A1 | 4/2010 |
| WO | 2013116839 A1 | 8/2013 |

OTHER PUBLICATIONS

International Search Report dated May 30, 2014 for corresponding PCT Application No. PCT/US2014/011267.
(Continued)

*Primary Examiner* — Michael L Hobbs
(74) *Attorney, Agent, or Firm* — Greenberg Traurig, LLP

(57) ABSTRACT

A method for processing a biological material sample includes dispensing a sample into wells of an array tape from a sample plate, dispensing a reagent into the wells of the array tape from a reagent plate, and sealing the sample and the reagent in the array tape. The method further includes
(Continued)

cooling the array tape and detecting biological material in the wells of the array tape.

5 Claims, 5 Drawing Sheets

(51) Int. Cl.
*C12Q 1/6844* (2018.01)
*G01N 21/64* (2006.01)
*G01N 35/00* (2006.01)
*G01N 35/10* (2006.01)
*G01N 35/04* (2006.01)

(52) U.S. Cl.
CPC ... *G01N 21/6456* (2013.01); *G01N 35/00009* (2013.01); *B01J 2219/00313* (2013.01); *B01J 2219/00351* (2013.01); *B01J 2219/00495* (2013.01); *B01J 2219/00585* (2013.01); *B01J 2219/00722* (2013.01); *B01L 2200/142* (2013.01); *B01L 2300/0812* (2013.01); *B01L 2300/1822* (2013.01); *B01L 2300/1894* (2013.01); *G01N 2035/00356* (2013.01); *G01N 2035/0403* (2013.01); *G01N 2035/1034* (2013.01)

(58) Field of Classification Search
CPC ... B01J 2219/00722; B01J 2219/00495; B01L 2200/142; B01L 2300/1894; B01L 2300/00356; B01L 7/00; G01N 21/6456; G01N 35/0009; C12Q 1/6846; A63B 37/0043; A63B 37/0092; A63B 37/0075; A63B 37/0074; A63B 37/0076; A63B 37/02; A63B 37/003; A63B 37/0031; A63B 37/0039; A63B 37/0063; A63B 37/0064; A63B 37/0045; A63B 37/0062; A63B 37/0044; A63B 37/0051; A63B 37/0059; A63B 37/0068; A63B 37/0033; A63B 37/0087; A63B 37/0096; A63B 37/0046

See application file for complete search history.

(56) References Cited

U.S. PATENT DOCUMENTS

| 4,792,373 | A | * | 12/1988 | Hsei ..................... B29C 66/133 156/497 |
| 4,877,745 | A | | 10/1989 | Hayes et al. |
| 6,632,653 | B1 | | 10/2003 | Astle |
| 6,720,191 | B1 | * | 4/2004 | Goldstein ............ G01N 1/2813 422/50 |
| 6,878,345 | B1 | | 4/2005 | Astle |
| 7,329,039 | B2 | | 2/2008 | Laugharn, Jr. et al. |
| 8,008,091 | B2 | | 8/2011 | Higashino et al. |
| 8,062,592 | B2 | | 11/2011 | Ozawa et al. |
| 2002/0086319 | A1 | | 7/2002 | Ellson et al. |
| 2004/0071599 | A1 | | 4/2004 | Rusch et al. |
| 2004/0253624 | A1 | | 12/2004 | Smith et al. |
| 2005/0208509 | A1 | | 10/2005 | Horwath et al. |
| 2005/0260592 | A1 | | 11/2005 | Gumbrecht et al. |
| 2007/0036721 | A1 | * | 2/2007 | Zinn ................... A61K 49/0008 424/9.1 |
| 2007/0286770 | A1 | | 12/2007 | Magnant et al. |
| 2011/0152108 | A1 | | 6/2011 | Brenan et al. |

OTHER PUBLICATIONS

Australian Government, IP Australia; Examination Report No. 2, Issued in Connection to AU2014205166; dated Jun. 15, 2017; 5 pages; Australia.

The State Intellectual Property Office of the People's Republic of China; The First Office Action, issued in connection to Application No. CN201480004660.5; dated Apr. 3, 2018; 16 pages; China.

The State Intellectual Property Office of the People's Republic of China; The Second Office Action, Issued in connection to CN201480004660.5; dated Nov. 5, 2018; 14 pages; China.

* cited by examiner

BIOLOGICAL SAMPLE ANALYTICAL INSTRUMENT

BACKGROUND

The present invention relates to inline sample processing on Douglas Scientific's Nexar® platform, specifically thermal management of an array tape path and chemistry performed in the array tape.

The current array tape platform uses a traditional polymerase chain reaction (PCR)-based approach for single nucleotide polymorphism (SNP) detection. The Nexar® transfers the source and assay from microplates into array tape, seals the array tape, and accumulates the array tape on spools. The array tape containing nucleic acid samples is then transferred to a Soellex® or another competing water bath product and amplified through PCR using thermocycling. The samples are then often centrifuged in order to draw the samples to the bottom of the array tape wells. This process simultaneously helps to dry the array tape. Subsequently, the array tape is loaded onto a detection instrument, such as the Araya®, which detects SNP presence in the sample using fluorescent detection.

The current array tape platform requires three separate instruments, thus requiring manual transfer of tape spools between instruments. Furthermore, the Soellex® can take an hour or longer to complete the required thermocycling. Centrifugation also may add longer than an hour to the process. Additionally, the array tape is processed at ambient conditions prior to entering the reaction/amplification stage. There is a need for shortening the length of time it takes to process samples using the array tape platform. There is also a need for controlling the temperature of the array tape prior to initiating a secondary process such as PCR.

SUMMARY

A method for processing a biological material sample includes dispensing a sample into wells of an array tape from a sample plate, dispensing a reagent into the wells of the array tape from a reagent plate, and sealing the sample and the reagent in the array tape. The method further includes cooling the array tape and detecting biological material in the wells of the array tape.

An apparatus for processing a biological material sample includes a dispensing system for dispensing a sample and a reagent into a matrix of wells of a array tape and a sealing system for sealing the sample and the reagent in the tape. The sealing system includes a sealing mechanism and a cooling system for cooling the tape. The apparatus further includes an amplification and detection system for detecting biological material in the matrix wells of the tape.

DETAILED DESCRIPTION

Unlike current systems, an embodiment of the analytical instrument of the present invention is an expanded version of the Nexar®, able to perform all required functions of the process inline, starting with sample supply and ending with detection. The analytical instrument transfers samples and reagents from microplates into array tape, seals the array tape, accumulates and incubates the samples at a temperature required for the reaction taking place, and fluorescently detects Fluorescein amidite (FAM®), VIC®, and 6-Carboxyl-X-Rhodamine (ROX®), or any other suitable dyes or fluorescent compounds. With fluorescent detection of amplified products, single base differences may be distinguished.

In alternative embodiments, the analytical instrument may detect absorbance, radioactivity, or thermal activity. Additionally, the analytical instrument may be used for SNP detection, gene detection, or gene expression. The analytical instrument of the present invention may also be utilized for analysis of a number of different biological samples including cell growth analysis, non-amplification biological analysis, pH detection, colorometric analysis, enzyme-linked immunosorbent assay (ELISA), loop mediated isothermal amplification (LAMP), live organism analysis, protein analysis, high throughput screening, high content screening, water quality analysis, and food quality analysis.

Figure 1:
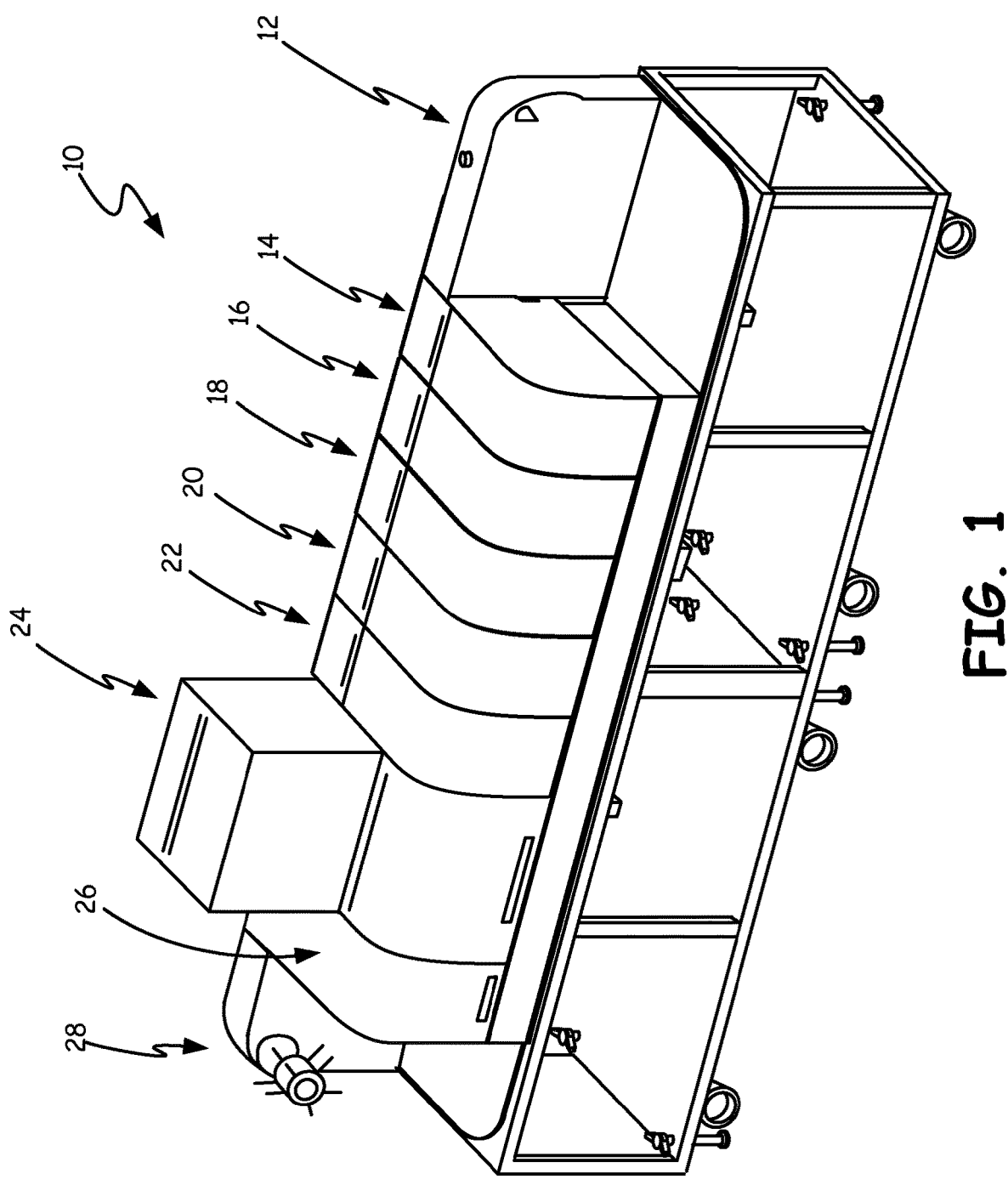
FIG. 1 is a perspective view of the analytical instrument of the present invention.
Figure 2:
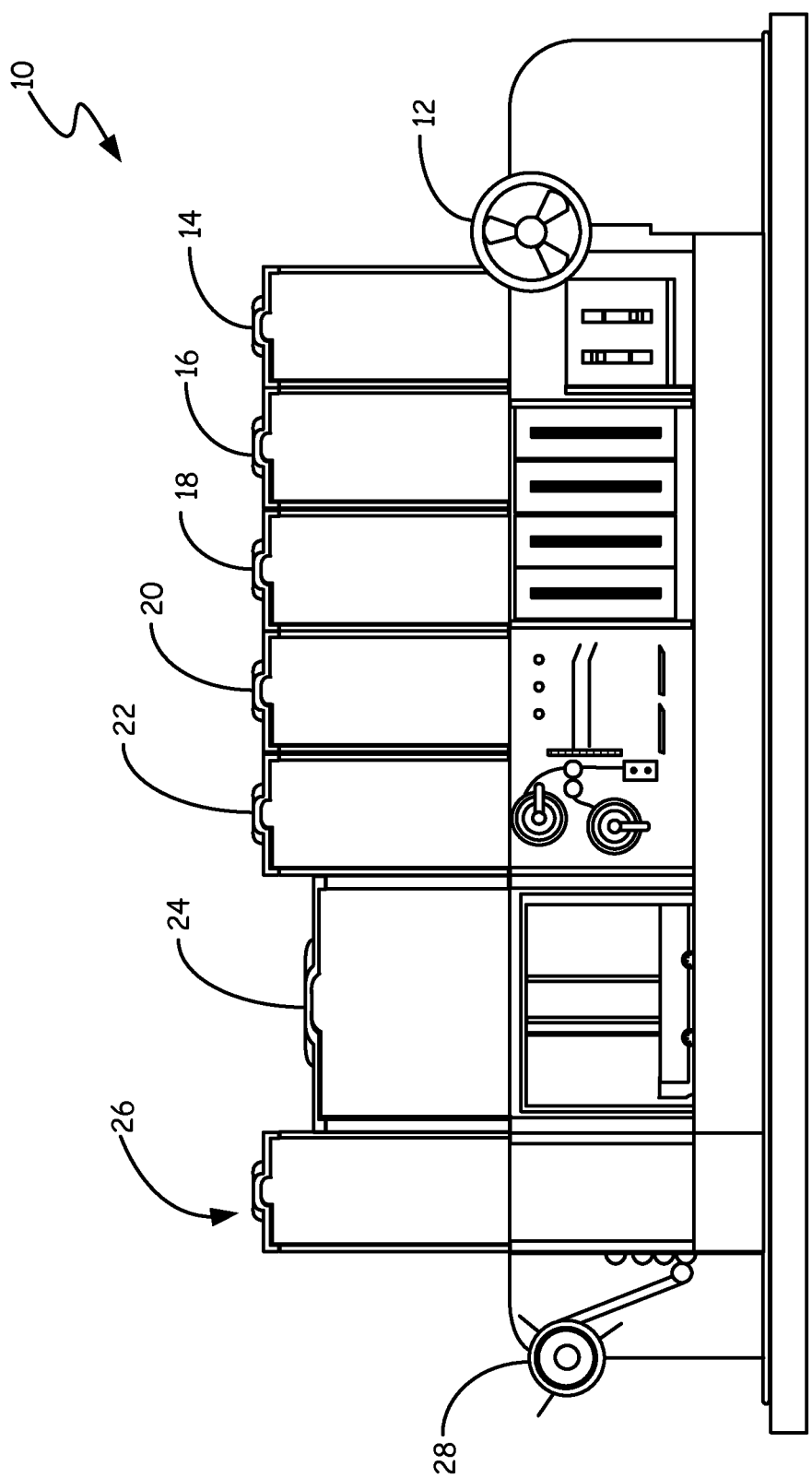
FIG. 2 is a front view of the analytical instrument with module covers open.

FIG. 1 is a perspective view of analytical instrument 10, with sample loading, processing, and detection all contained within the instrument, not requiring transfer of array tape during any of these steps. FIG. 2 is a front view of analytical instrument 10 with the module covers open, showing the details of each module. Analytical instrument 10 includes unwind module 12, sample dispensing module 14, sample plate stacker module 16, reagent plate stacker module 18, reagent dispensing module 20, tape sealer module 22, incubation/accumulation module 24, detection/imaging module 26, and rewind module 28. Analytical instrument 10 may include as many copies of each of modules 12-28 as necessary for the desired chemistry.

In the example embodiment, the inline process is performed reel-to-reel. In an alternative embodiment, the inline process may be performed reel to result followed by sample disposal. In other embodiments, the inline process may be performed using non-reel to reel array tape segments, using a cassette, or using singulated samples. The array tape of analytical instrument 10 may progress linearly through analytical instrument 10 or may also backtrack if required for the desired chemistry. The array tape format for analytical instrument 10 may include thermoformed wells or any other kind of array tape suitable for the application.

Referring to FIGS. 1 and 2, biological sample processing in analytical instrument 10 begins with unwind module 12. Unwind module 12 unrolls the array tape to prepare it for sample loading in sample dispensing module 14. In sample dispensing module 14, a pipettor is used to transfer samples from microplates containing the samples to the array tape. Sample plate stacker module 16 allows multiple microplates to be prepared for sample loading onto the array tape. In an alternative embodiment, the array tape for analytical instrument 10 is pre-loaded with samples that may be lyophilized.

After samples are loaded into the wells of the array tape, the array tape proceeds to reagent dispensing module 20, where reagents stored in reagent plate stacker module 18 necessary to carry out the desired chemical reaction are added to the samples. Reagent dispensing module 20 may include a dispensing jet. In alternative embodiment, reagent dispensing module 20 may include a reservoir dispenser with or without temperature control, or a contact-to-dispense system. Reagent dispensing module 20 may also include filtration in order to prevent contamination of the samples in the array tape wells. Reagent dispensing module 20 may also include humidity control. In an alternative embodiment, every module, including reagent dispensing module 20, may include environmental control, such as humidity control or filtration.

In one embodiment, sample dispensing module 14, sample plate stacker module 16, reagent plate stacker module 18, and reagent dispensing module 20 may all include heating or cooling to keep reagents and samples at a desired temperature. In an alternative embodiment, each individual module may include its own heating or cooling system. In another embodiment, as the array tape is processed through analytical instrument 10, a cover plate may be used to enhance thermal transfer to the array tape to maintain the chemistry at a desired temperature. In other embodiments, each module may include a Peltier plate for thermal regulation of the tape as it passes through the module or suitable heating or cooling elements may be incorporated into the array tape for thermal regulation of the array tape as it passes through each module. Alternatively, each entire module enclosure may be thermally regulated. Thermal regulation may be provided using a heat exchanger, a Peltier block, microwaves, resistive elements, liquid nitrogen, a refrigeration unit, heating or cooling vents, or infrared elements.

After reagent addition, the array tape advances to tape sealer module 22. Tape sealer module 22 provides thermal management of the array tape using a thermoelectric attachment that cools the tape path to lower than 20 degrees Celsius. The thermoelectric attachment maintains the tape path at a user defined temperature between ambient temperature and 4 degrees Celsius. Cooling the chemistry in the array tape wells inhibits any reaction that may take place at room temperature from taking place until the array tape enters incubation/accumulation module 24. Cooling the chemistry also prevents evaporation of the chemistry, resulting in poor reaction performance. In one embodiment, cooling is provided with a Peltier plate. In alternative embodiments, both heating up to 120 degrees Celsius and cooling down to −30 degrees Celsius may be provided with a liquid circulation plate or other suitable alternatives. In an alternative embodiment, if only heating is required, a conventional resistive heater may be used.

After the array tape is sealed and cooled or heated to a desired temperature, the array tape proceeds to incubation/accumulation module 24. Incubation/accumulation module 24 includes a path, such as a serpentine path, for the array tape. This path allows multiple arrays to accumulate in the incubation/accumulation module 24. Incubation/accumulation module 24 provides heat, if necessary, using blowers with heater paths or other suitable alternatives. In an alternative embodiment incubation/accumulation module 24 provides cooling if required for the reaction taking place. Incubation/accumulation module 24 may maintain a temperature from ambient to 70 degrees. In alternative embodiments, incubation/accumulation module 24 may maintain heating up to 120 degrees Celsius and cooling down to −30 degrees Celsius. The temperature maintained in incubation/accumulation 24 module depends on the requirements of the reaction that is taking place.

In one embodiment, the reaction carried out in incubation/accumulation module 24 is EnviroLogix's DNAble® chemistry, which employs an isothermal amplification process, which eliminates the need for thermocycling as a means to amplify nucleic acid products for endpoint detection. The reaction proceeds at a single, elevated temperature, usually 56 degrees Celsius. DNAble® chemistry allows adequate amplification to be completed in less than ten minutes.

In an alternative embodiment, the reaction carried out in incubation/accumulation module 24 may be used for Salmonella detection. The reaction begins at room temperature, so the Peltier plate cooling provided by the tape sealer module will prevent the reaction from taking place until the array tape is in the accumulation/incubation module. Once in incubation/accumulation module 24, if employing, for example, TwistGlow™ Salmonella chemistry, the reaction proceeds at 40 degrees Celsius and is complete in approximately ten minutes. Alternatively, Se Gene-DART chemistry may be used, where the reaction proceeds at 65 degrees Celsius for 30 minutes. In alternative embodiments, any other suitable biological reactions may be carried out.

Once the reaction is complete in incubation/accumulation 24 module, the array tape proceeds to detection/imaging module 26, which may include a scanning rail with an optical reader. In one embodiment, a detection instrument, such as the Araya®, scans one column of the sample array at a time. The detection/imaging module 26 may fluorescently detect FAM®, VIC®, and ROX®, and other fluorescent compounds or dyes. With fluorescent detection of amplified products, single base differences can be distinguished. Detection/imaging module 26 may include a charged coupled device (CCD), a photo multiplier tube (PMT), or a photon counter.

In alternative embodiments, detection/imaging module 26 may detect absorbance, radioactivity, or thermal activity. Additionally, detection/imaging module 26 may be used for SNP detection, gene detection, or gene expression. Detection/imaging module 26 may also be utilized for analysis of a number of different biological samples including cell growth analysis, non-amplification biological analysis, pH detection, colometric analysis, enzyme-linked immunosorbent assay (ELISA), live organism analysis, protein analysis, high throughput screening, high content screening, water quality analysis, and food quality analysis. Once detection is complete for an entire array, the array tape advances, the scanned array is rewound via rewind module 28, and detection/imaging module 26 proceeds to scan the next array on the array tape.

While the example embodiment includes accumulation/incubation module 24, in an alternative embodiment, analytical instrument 10 may perform real time PCR (qPCR) simultaneously with detection. Amplification using qPCR may take between 30 seconds and 2 hours to complete. This embodiment does not require incubation/accumulation module 24, and detection/imaging module 26 may have the capability to scan the entire array of wells on the array tape, instead of one column at a time. Detection/imaging module 26 may further include a Peltier plate to allow both isothermal heating and thermocycling of the array as necessary for the chemistry.

Figure 3:
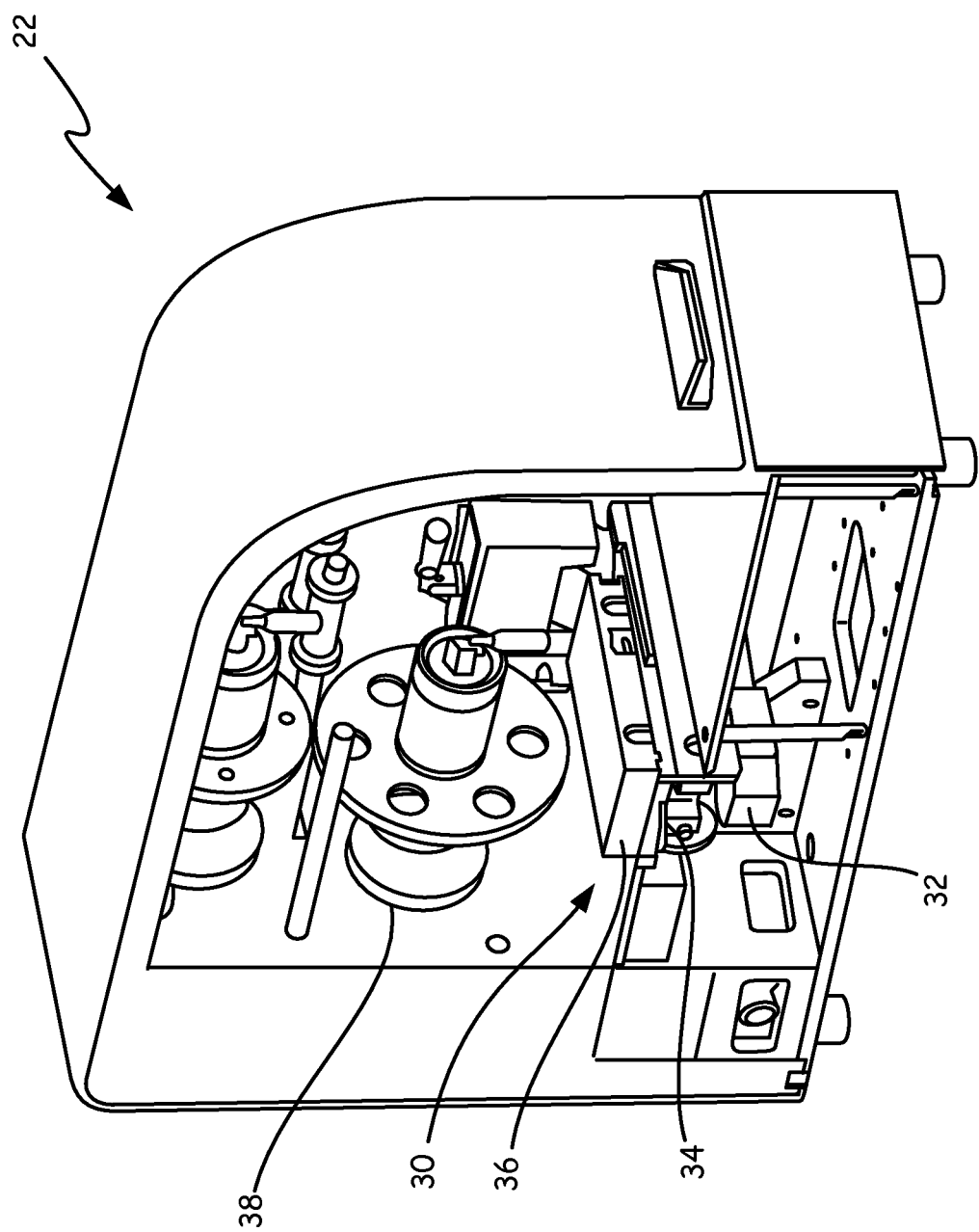
FIG. 3 is a perspective view of the sealing module of the analytical instrument.
Figure 4:
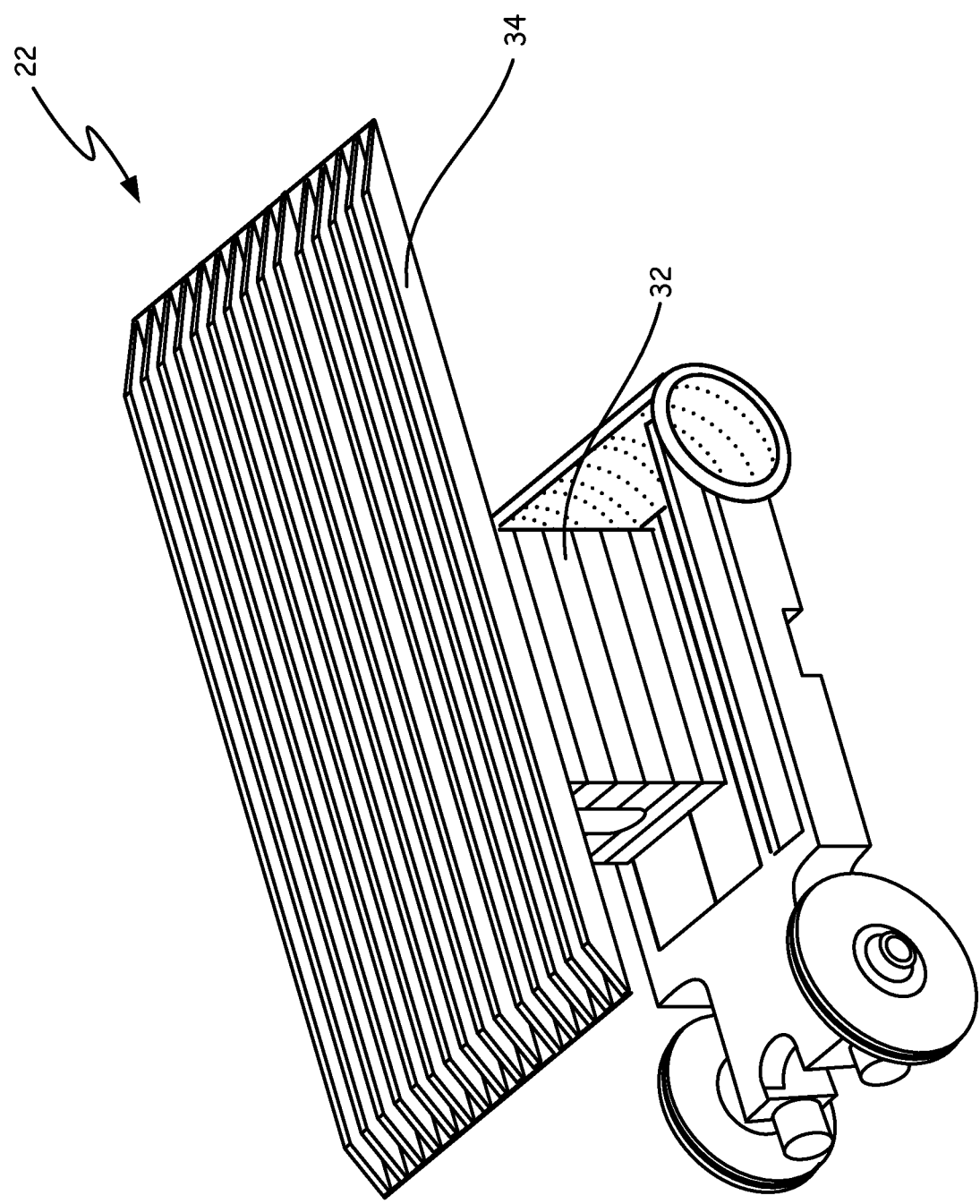
FIG. 4 is a perspective view of the thermoelectric assembly of the sealing module.
Figure 5:
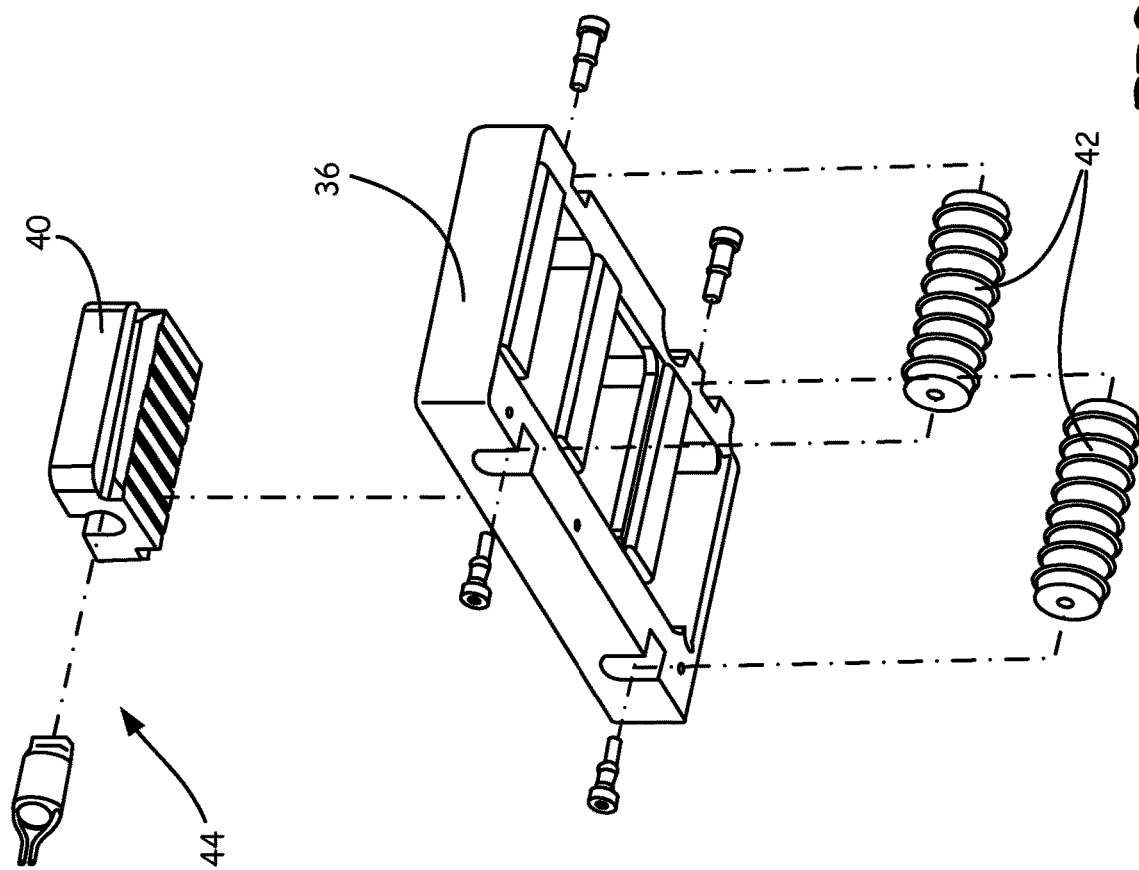
FIG. 5 is an exploded view of the pressure plate of the thermoelectric assembly of the sealing module.

FIG. 3 is a perspective view of sealing module 22, including thermoelectric assembly 30 with Peltier plate 32 installed beneath groove plate 34 and groove plate 34 under pressure plate 36. Tape sealing mechanism 38 is above groove plate 34. FIG. 4 is a perspective view of thermoelectric assembly 30 without pressure plate 36. Peltier plate 32 is installed beneath groove plate 34, allowing cooling or heating of the sample as the array tape is sealed. FIG. 5 is an exploded view of pressure plate 36 with mixer attachment 40. In an alternative embodiment, groove plate 34 may be replaced with any suitable plate compatible with the desired array tape format.

Referring to FIGS. 3-5, thermoelectric attachment 30 includes Peltier plate 32 mounted directly to the underside of groove plate 34. Peltier plate 32 supplies cooling via conduction and convection as the array tape moves over groove plate 34 and while the array tape is stopped. Thermal transfer to the array tape occurs when a weighted roller pushes the array tape to groove plate 34 in order to seal the array tape to prepare the array tape for incubation. Peltier plate 32 may chill groove plate 34 to as low as 4 degrees Celsius. This results in an array tape temperature of approximately 7 degrees Celsius. In alternative embodiments, Peltier plate 32 may provide heating up to 120 degrees Celsius or cooling down to −30 degrees Celsius, depending on the requirements of the chemistry in the array tape.

In an alternative embodiment, insulated pressure plate 36 may provide additional pressure to the array tape, improving thermal conduction. Pressure plate 36 uses rollers 42 to allow the array tape to move freely under the plate while maintaining pressure at the array tape/groove plate 34 interface. Pressure plate 36 may be adapted to receive mixer attachment 40 with electrical motor and eccentric cam 44 to vibrate the array tape for mixing enhancement within the wells of the array tape. The motor speed and eccentric cam weight of electrical motor and eccentric cam 44 may be varied in order to provide more or less vibration. The mix area may be varied from one column to the entire array using a flat foot interface. Furthermore, mixing may occur continuously or while the array is in motion.

While the above-identified drawing figures set forth one or more embodiments of the invention, other embodiments are also contemplated. In all cases, this disclosure presents the invention by way of representation and not limitation. It should be understood that numerous other modifications and embodiments can be devised by those skilled in the art, which fall within the scope and spirit of the principles of the invention. The figures may not be drawn to scale, and applications and embodiments of the present invention may include features and components not specifically shown in the drawings.

Any relative terms or terms of degree used herein, such as "substantially", "essentially", "generally" and the like, should be interpreted in accordance with and subject to any applicable definitions or limits expressly stated herein. In all instances, any relative terms or terms of degree used herein should be interpreted to broadly encompass any relevant disclosed embodiments as well as such ranges or variations as would be understood by a person of ordinary skill in the art in view of the entirety of the present disclosure, such as to encompass ordinary manufacturing tolerance variations, incidental alignment variations, alignment or shape variations induced by operational conditions, and the like.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the spirit and scope of the present disclosure, viewed in its entirety.

The invention claimed is:

1. An apparatus for processing a biological material sample, the apparatus comprising:
    a dispensing system configured and arranged for dispensing a sample and a reagent into a matrix of wells of a tape;
    a sealing system configured and arranged for sealing the sample and the reagent in the tape, the sealing system comprising:
        a sealing mechanism located adjacent a cooling system,
        the cooling system positioned directly below the sealing mechanism on an opposite side of the tape from the sealing mechanism, the cooling system, configured and arranged for cooling the sample as the tape is sealed by the sealing mechanism; and
    an amplification and detection system for detecting biological material in the matrix of wells of the tape; and
    wherein the cooling system comprises a Peltier plate mounted directly to the underside of a groove plate, the Peltier plate configured and arranged to supply cooling via conduction and convection as the tape moves over the groove plate and while the tape is stopped.

2. An apparatus for processing a biological material sample, the apparatus comprising:
    a dispensing system configured and arranged for dispensing a sample and a reagent into a matrix of wells of a tape;
    a sealing system configured and arranged for sealing the sample and the reagent in the tape, the sealing system comprising:
        a sealing mechanism located adjacent a cooling system,
        the cooling system positioned directly below the sealing mechanism on an opposite side of the tape from the sealing mechanism, the cooling system, configured and arranged for cooling the sample as the tape is sealed by the sealing mechanism; and
    wherein the sealing mechanism comprises a weighted roller, wherein thermal transfer between the tape and the cooling system occurs when the weighted roller pushes the tape to a groove plate to seal the tape in preparation for incubation.

3. The apparatus of claim 2, wherein the sealing system further comprises a pressure plate configured to provide additional pressure to the tape and improve thermal conduction between the tape and the cooling system.

4. The apparatus of claim 3, wherein the pressure plate comprises rollers, the rollers configured to allow the tape to move freely under the pressure plate while maintaining pressure at an interface including the tape and groove plate.

5. The apparatus of claim 3, wherein the pressure plate is configured to be adapted to receive a mixer attachment, the mixer attachment including an electrical motor and eccentric cam configured to vibrate the tape providing mixing enhancement within the wells of the tape.

* * * * *